United States Patent
Yock

Patent Number: 5,311,871
Date of Patent: May 17, 1994

[54] SYRINGE WITH ULTRASOUND EMITTING TRANSDUCER FOR FLOW-DIRECTED CANNULATION OF ARTERIES AND VEINS

[76] Inventor: Paul G. Yock, 2200 Redington Rd., Hillsborough, Calif. 94010

[21] Appl. No.: 3,203

[22] Filed: Jan. 12, 1993

[51] Int. Cl.⁵ ............................................. A61B 8/12
[52] U.S. Cl. ........................... 128/662.95; 128/663.01
[58] Field of Search ................... 128/662.05, 662.06, 128/661.09, 663.01; 604/116, 117

[56] References Cited

U.S. PATENT DOCUMENTS

| | | | |
|---|---|---|---|
| 4,852,575 | 8/1989 | Nikoonahad | 128/663.01 |
| 4,887,606 | 12/1989 | Yock et al. | 128/662.05 |
| 5,080,103 | 1/1992 | Olivier | 128/662.05 |
| 5,080,104 | 1/1992 | Marks et al. | 128/662.05 |

*Primary Examiner*—William E. Kamm
*Assistant Examiner*—George Manuel
*Attorney, Agent, or Firm*—Dykema Gossett

[57] ABSTRACT

A needle and syringe assembly including a transducer for directing ultrasonic waves through the needle and receiving reflected ultrasonic waves through the needle as the needle is inserted into tissue. The ultrasonic transducer has a surface area which substantially equals the surface area of the plunger head within the syringe body to permit the delivery of more power and thereby increase the depth of penetration of the transmitted and reflected waves. A lens may be associated with the transducer for focusing ultrasonic waves from the transducer through the needle. Further, the transducer may include a plurality of sections or portions in a planar arrangement to permit either continuous wave or pulsed wave transmission and reception of the ultrasonic energy passing through the needle. The plunger, transducer, and lens may be detachable from the syringe body and needle whereby the assembly can be reusable and can be employed with conventional syringes and needles when only ultrasonic guidance of the needle is required. In another embodiment, a pod assembly, which houses the transducer and lens, is detachably connected between the needle and syringe cylinder. the detachable pod assembly permits cleansing and sterilization of the transducer and lens for reuse with disposable needles and syringes.

11 Claims, 2 Drawing Sheets

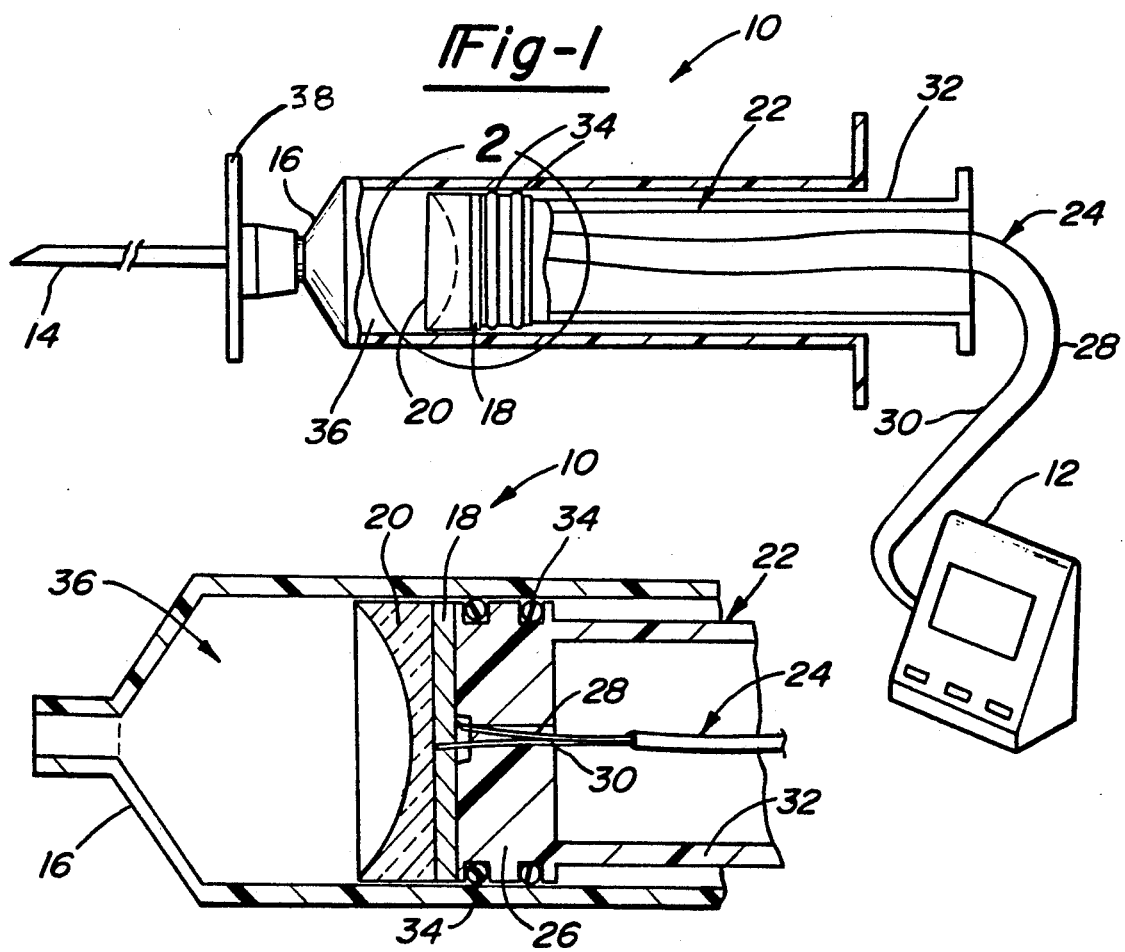
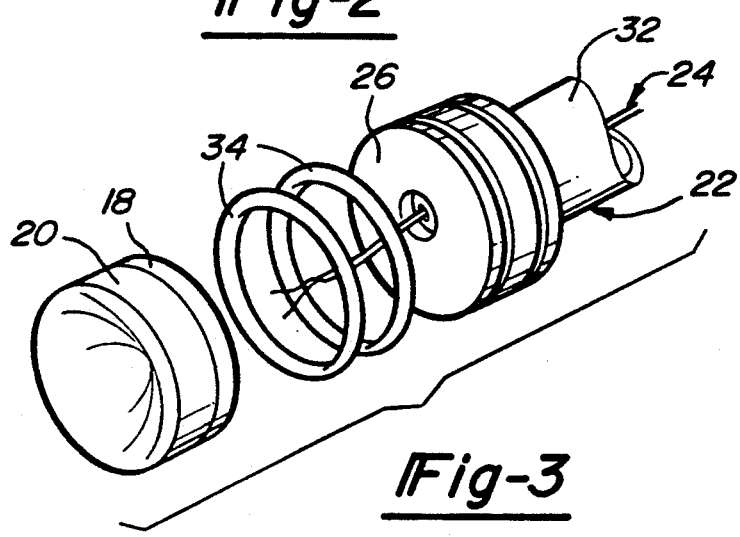

SYRINGE WITH ULTRASOUND EMITTING TRANSDUCER FOR FLOW-DIRECTED CANNULATION OF ARTERIES AND VEINS

TECHNICAL FIELD OF THE INVENTION

The present invention relates generally to cannulation of arteries and veins, and more particularly, the invention relates to the use of ultrasonic techniques for flow directed cannulation.

BACKGROUND OF THE INVENTION

Insertion of arterial and venous catheters for angiography and acute care of patients is a major source of discomfort, morbidity, and even mortality. The problem of accurate location and penetration of arteries and veins is especially acute for patients who may be obese or present unusual anatomy and who are undergoing cardiac catheterization and other radiological procedures such as cerebral angiograms.

To avoid difficulties when localizing the vessel and to reduce the risk of complications, it is known to determine the position and the course of the vessel to be penetrated by means of ultrasonic Doppler sonography. Known apparatus emits an ultrasonic beam from the skin surface toward the interior of the body. If any blood vessels are present within this ultrasonic beam, the emitted wave undergoes a Doppler effect due to flow through the blood vessels or the pulsation of the vascular walls, so that a reflected wave that has a different frequency from that of the emitted wave can be obtained.

After this reflected wave has been converted into an electrical signal with an ultrasonic oscillator, synthetic detection of the emitted signal allows an electric signal of the difference of the two waves to be obtained. This can be amplified and sent to a speaker or the like to produce a sound having a unique tone that can be detected by the ear. These sounds reach their maximum volume when the ultrasonic beam is directed toward the center of the artery or vein in question and cease if the ultrasonic beam strays from the vessel. Further, the reflected wave from tissue that has no movement cannot be heard nor can the sound resulting from vessels that are out of the line of the beam. Hence, Doppler sonography provides a simple means of localizing vessels both easily and accurately.

The potential utility of Doppler ultrasound for accurately guiding a needle into a vessel has been recognized. Most applications utilize the transmission of ultrasonic waves through the needle and reception of ultrasonic echoes by a separate transducer located on the body of the patient and separate from the syringe and needle. Such applications obviously have limited accuracy. U.S. Pat. No. 3,556,079 for "Method of Puncturing A Medical Instrument Under Guidance of Ultrasound" discloses in one embodiment the placement of both transmitting and receiving transducers in the needle and syringe. Such an embodiment, however, requires a special catheter construction and can give an erroneous signal when the needle engages the blood vessel before penetrating the vessel.

A major advance to Doppler technology was made by virtue of U.S. Pat. No. 4,887,606 directed to an "Apparatus for Use In Cannulation of Blood Vessel", which teaches the use of a transducer insert positioned within a hollow needle including an ultrasonic transducer at one end for transmitting and receiving ultrasonic waves through the sharpened end of the needle. Upon location and penetration of a blood vessel, the transducer insert is removable from the needle for implementation of the known Seldinger technique for placing a catheter in a blood vessel. Although the device disclosed in U.S. Pat. No. 4,887,606, the disclosure of which is incorporated by reference herein, represents a superior apparatus for cannulation of blood vessels, such apparatus could be improved upon. For example, the power emitted by a transmitting transducer is at least in part a function of surface area. Thus, larger surface area transducers can deliver more power and thereby increase the depth of penetration of the transmitted and reflected waves.

Since the reflected waves from small vessels that are located at large depths from the surface of the body are weak, it is important in certain applications to increase the depth of penetration of the transmitted and reflected waves. Therefore, there has been a need for an improved apparatus for the cannulation of blood vessels in certain applications.

SUMMARY OF THE INVENTION

The present invention provides an apparatus including a transmitting and receiving transducer which is located either adjacent to the syringe plunger such that it is movable therewith or at a position affixed to the inner wall of the syringe body or in a pod assembly between the syringe body and the introducer needle. In the first embodiment, the transducer is sandwiched between the end of the plunger and an acoustic lens which assists in focusing the ultrasonic beam. The head of the plunger assembly includes one or more sterile seals thereby permitting introduction of the plunger assembly, transducer, and lens into a regular syringe body or cylinder. In this way, the syringe cylinder becomes a disposable sleeve which can be thrown away after each use. In the latter embodiment, the pod assembly, which houses the transducer and lens, is retained and reused while the syringe cylinder and needle may be disposed of after each use.

In the first embodiment, a generally hollow body portion supports the head of the plunger assembly. This permits electrical connection between the transducer and a transmitting and receiving apparatus within an audio monitor. Saline solution is aspirated into the introducer needle such that no air is present. After penetrating the skin subcutaneously, a small amount of the saline solution in the syringe is injected and the physician proceeds to sweep the needle in a circular motion to scan for the vessel to be accessed. When the needle is pointing towards a moving medium such as blood flow, an audio signal is generated, as is conventional, from the audio monitor. The physician then advances the needle in the direction that intensifies the signal until the needle punctures the vessel wall for access. In this way, it is possible to accurately locate and penetrate vessels located in deeper layers.

The introducer needle is similar to the device disclosed in U.S. Pat. No. 4,887,606. However, as described above, the transducer in the present invention is not positioned within the hollow needle but instead is positioned within the enlarged cylindrical body of the syringe. Further, the audio monitor is a combined transmitting apparatus and receiving apparatus within a single housing. The transmitting apparatus portion of the audio monitor includes an oscillator for exciting the ultrasonic transducer that is located inside the syringe.

The receiving circuit portion of the audio monitor also includes an oscillator and circuitry for receiving the reflected ultrasonic waves whereby an electrical signal of audiofrequency is obtained which can be heard as an audible sound having a unique tone. The electrical components of the audio monitor are conventional and do not by themselves form any part of the present invention.

In another embodiment of the invention, a pod assembly is detachably mounted at its opposite ends to a regular syringe body and to a conventional needle. The pod assembly houses the transducer and lens such that the pod assembly and its contents may be reused while the syringe and needle may be disposed of after each use. With this embodiment, the transducer and lens can be cleaned and sterilized for reuse with disposable conventional needles and syringes. Thus, the pod assembly may be included when ultrasonic guidance is required in locating an artery or vein.

The invention and objects and features thereof will be further apparent from the following detailed description and the appended claims when taken with the drawings.

BRIEF DESCRIPTION OF THE DRAWINGS

FIG. 1 is an overall view of the needle and syringe assembly which is made in accordance with the present invention.

FIG. 2 is a cross-sectional longitudinal view of the syringe body.

FIG. 3 is a perspective assembly view of the plunger assembly, transducer, and acoustic lens.

DETAILED DESCRIPTION OF THE INVENTION

Figure 4:
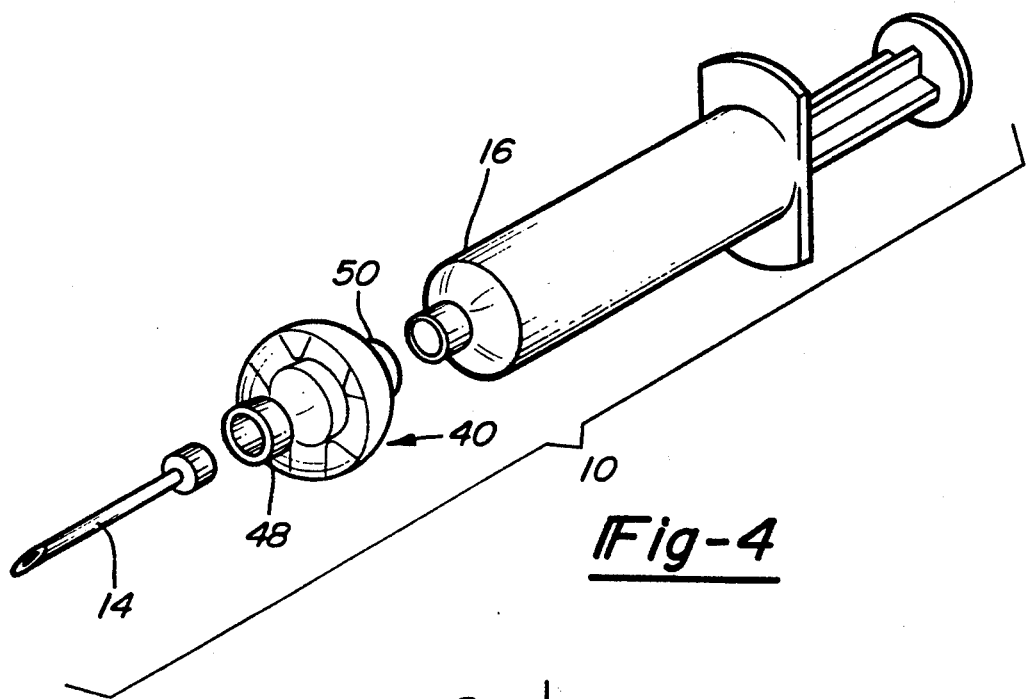
FIG. 4 is a perspective assembly view of another embodiment of the needle and syringe assembly which is made in accordance with the present invention.

With reference to FIG. 1, a schematic illustration of the needle and syringe assembly 10 and audio monitor 12 is shown. The assembly 10 includes an introducer needle 14 that is connected to a disposable cylindrical syringe body 16. The syringe body 16 provides a housing for ultrasonic transducer 18, acoustic lens 20, and plunger assembly 22.

An electrical connection 24 is provided between transducer 18 and audio monitor 12 for the transmission and reception of signals as the needle 14 is inserted through tissue towards a blood vessel. As described above, the insertion of arterial and venous catheters can be a major source of discomfort, morbidity, or even mortality. The assembly in accordance with the present invention and the method of using the assembly provides accurate direction of the needle 14 into a blood vessel. As the needle 14 is passed through tissue, the tip of the needle is moved in a slight arc for directing ultrasonic sound energy transmitted through the needle to a blood vessel. The returned echo signal is used for accurately guiding the needle 14 to the vessel and may provide an indication of when the needle penetrates the vessel.

The intensity of the Doppler signal versus depth within tissue is explained in U.S. Pat. No. 4,887,606. When needle 14 is first inserted into the tissue but not directed towards an artery or vein, the response is small and relatively flat. Upon pointing the needle at an artery, an increased modulated wave is detected, and conversely when the needle is pointed towards a vein, an increased generally uniform signal is detected. As the needle is advanced towards the artery or vein, the intensity of the reflected wave increases, and upon penetration of the vessel a stepped increase in the intensity of the reflected signal is indicated.

Actual penetration of a blood vessel will be indicated by the back flow of blood when the vessel is penetrated by maintaining a negative pressure in the needle and constant back pressure on the syringe while the needle is being advanced. Once the vessel is penetrated, brisk back flow of blood in the needle indicates safe penetration of the vessel and can cause the stepped increase in reflected wave intensity thereby indicating a safe location for injection of medications or passage of a wire into the vessel. The syringe body 16 is made of a clear plastic or glass to visually assess back flow once penetration of the needle 14 into the vessel is achieved.

FIG. 1-3 are illustrative of apparatus for use in cannulation of blood vessels in accordance with the present invention. The ultrasonic transducer 18 is shown affixed to the head portion 26 of plunger assembly 22 by means of a low impedance epoxy which is filled with glass microballoons, as disclosed in U.S. Pat. No. 4,887,606. The transducer 18 has a surface area which substantially equals the surface area of plunger head 26 to permit the delivery of more power. A conductor 28 from electrical connection 24 extends into contact with an electrode on the back surface of transducer 18. Another electrical conductor 30 from electrical connection 24 extends into contact with an electrode on the front surface of transducer 18. The conductors 28 and 30 form the coaxial electrical connection 24 between audio monitor 12 and transducer 18. Audio monitor 12 is a combined transmitting apparatus and receiving apparatus within a single housing. The transmitting apparatus (not shown) is a conventional oscillator which is used to excite the transducer. Similarly, the receiving apparatus and related circuity (not shown) comprises an oscillator and related circuity for receiving the reflected ultrasonic waves and transmitting an electrical signal to a speaker or the like to produce a characteristic sound. As is conventional, the transmitted waves undergo a Doppler effect due to the movement of the corpuscles flowing through a blood vessel or the pulsation of the vascular wall, so that the reflected wave has a different frequency from that of the transmitted wave. After the reflected wave has been converted into an electrical signal with an ultrasonic oscillator, the resulting signal is sent to a speaker so that the distinctive sound can be detected by ear. The basic components of the audio monitor 12 and their operation are conventional. The disclosure U.S. Pat. No. 3,556,079 is incorporated herein with respect to the conventional components used in audio monitor 12.

The plunger assembly 22 includes a head portion 26 for supporting transducer 18 and a manually movable cylindrical portion 32 which is generally hollow to permit passage of conductors 28 and 30 therethrough. The plunger head 26 includes one or more sterile radial seals 34 which are flexible to permit removal of the entire assembly. In this way, the plunger assembly can be introduced into the disposable syringe body or sleeve 16 and can be manipulated for use. After use, the plunger assembly 22 may be removed from the cylindrical sleeve or body 16 such that the sterile disposable sleeve 16 of the syringe may be thrown away after each use.

The acoustic lens 20 is affixed to transducer 18 for focusing the ultrasonic beams emitted from the transducer. Standard saline solution is aspirated into the open cavity 36 of syringe body 16 such that no air is present between the transducer 18 and the tip of the introducer needle 14. The apparatus for cannulation of blood vessels as described above is readily utilized in the Seldinger technique for blood vessel cannulation. After the aspirated needle is advanced subcutaneously, the physician proceeds to sweep the needle 14 in a circular motion to scan for the blood vessel to be accessed. When the needle is pointing towards the blood vessel, an audio signal will be heard from the audio monitor 12. The physician advances the needle 14 in the direction that intensifies the signal until the needle punctures the vessel wall and makes access. After the vessel is penetrated, there is a back flow of blood through the needle 14 into the cavity 36. The syringe body 16 is then removed from needle 14 by means of releasable connector 38. As is conventional a wire is placed through the needle 14 into the vessel, and the needle is then removed. Finally, a prothesis is guided into position in the vessel by the wire and the wire is then removed.

Thus, the present construction permits a larger sized transducer 18 which can deliver more power and thereby increase the depth of penetration of the transmitted and reflected ultrasonic waves. Further, since one of the primary indicators of vascular access is the flow of blood back into the needle (flashback) the elimination of a probe within the inner lumen of the introducer needle 14 provides a free and clear passage to cavity 26 for maximizing the amount of flashback. Moreover, the use of a curved acoustic lens 20 and saline solution interface between the transducer and end of needle 14 provides improved propagation of the ultrasonic waves transmitted and received by the transducer.

While the invention has been described with reference to specific embodiments, the description is illustrative of the invention and is not to be construed as limiting the invention. Various modifications and applications may occur to those skilled in the art without departing from the scope of the invention. For example, the transducer 18 could comprise a multi-part or piece assembly or array of transducer portions in a planar arrangement (not shown) for both transmitting and receiving the ultrasonic waves. That is, portions of the transducer could act as transmitters and portions of the transducer could act as receivers whereby the combined effect permits continuous wave transmission and reception of ultrasonic energy passing through needle 14. Further, transducer 18 and lens 20 may be affixed to the inner periphery of body 16 (not shown) wherein a central opening (not shown) is provided through the transducer and lens to permit communication of fluid between needle 14 and plunger head 26. In this embodiment, the electrical conductors 28 and 30 would be affixed to the sidewalls of body 16 for attachment to the front and back faces of transducer 18, as previously described. Alternatively, openings could be provided around the perimeter of the transducer 18 and lens 20 (through appropriate support structure connected to the inner periphery of sleeve 16) so that the central portion of the lens and transducer can be utilized for the transmission and reception of ultrasonic energy.

Figure 5:
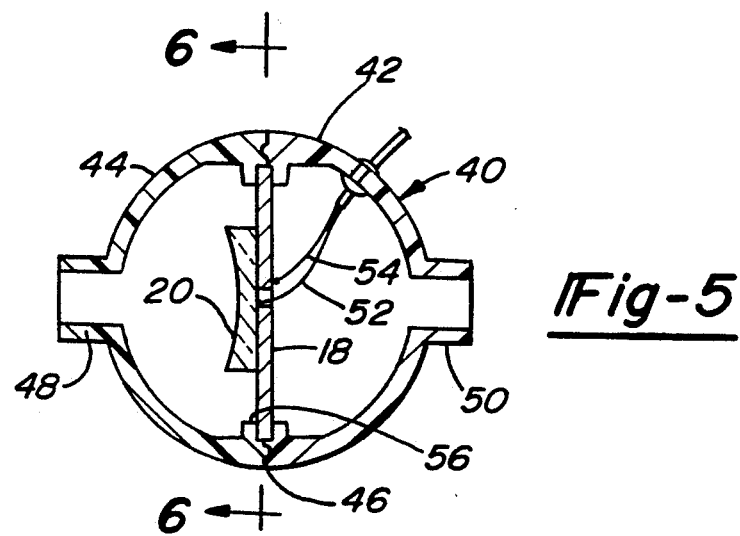
FIG. 5 is a longitudinal cross-section through the pod assembly shown in the embodiment of FIG. 4.
Figure 6:
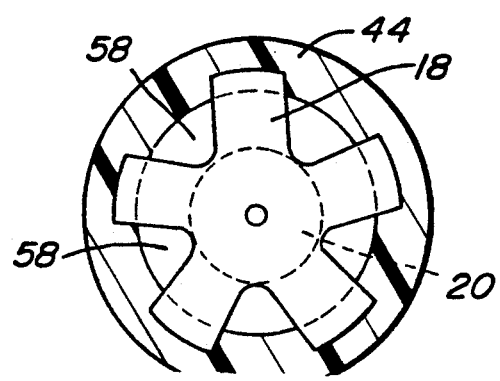
FIG. 6 is a cross-sectional view taken along line 6—6 in FIG. 5.

FIGS. 4-6 are illustrative of another embodiment of the apparatus for use in cannulation of blood vessels in accordance with the present invention. A pod assembly 40, which houses ultrasonic transducer 18 and acoustic lens 20, is detachably connected to needle 14 and syringe body 16. Pod assembly 40 includes separable, symmetrical portions 42 and 44 which are separable along a marginal edge 46. One end 48 of pod assembly 40 is detachably connected to needle 14 while the opposite end 50 of assembly 40 is detachably connected to syringe body 16. Electrical connections 52 and 54 are provided between transducer 18 and an audio monitor 12, as previously described for the prior embodiments. Conductor 52 extends into contact with an electrode on the front surface of transducer 18 while conductor 54 extends into contact with an electrode on the back surface of transducer 18.

Pod portions 42 and 44 include inwardly directed lip edges 56 which sandwich transducer 18 therebetween. As illustrated, acoustic lens 20 is centrally affixed to transducer 18 with openings 58 being provided around the perimeter of transducer 18 to permit communication of fluid between syringe 16 and needle 14. Since the pod assembly 40 is detachable from needle 14 and syringe 16, transducer 18 and lens 20 can be cleaned and sterilized for reuse with disposable needles and syringes.

I claim:
1. A needle and syringe assembly comprising:
   a needle, a syringe means, and a releasable connector between said needle and syringe means;
   said syringe means including a body having an inner surface;
   plunger means movable within said body and an ultrasonic transducer positioned adjacent one end of said plunger means with means for transmitting and receiving ultrasonic waves; and
   the surface area of said transducer being substantially greater than the cross-sectional area of said needle.
2. The needle and syringe assembly as defined in claim 1 including means for directing the ultrasonic waves from said transducer through said needle.
3. The needle and syringe assembly as defined in claim 2 wherein said directing means includes a curved lens means positioned adjacent to said transducer.
4. The needle and syringe assembly as defined in claim 1 including electrical connection means wherein said electrical connection means is connected between said transducer and an audio monitor, and wherein said audio monitor transmits electrical signals to and receives electrical signals from said transducer.
5. The needle and syringe assembly as defined in claim 1 wherein said plunger means includes seal means in engagement with said inner surface for permitting removal of said plunger means and transducer from said syringe body wherein said syringe body is disposable after use.
6. The needle and syringe assembly as defined in claim 1 wherein said transducer comprises a plurality of transducer portions.
7. The needle and syringe assembly as defined in claim 1 wherein said transducer is attached to said inner surface.
8. A needle and syringe assembly comprising:
   a needle having a connector portion and a syringe means having a connector portion;
   a pod assembly detachably mounted to said needle and syringe means between said connector portions; and an ultrasonic transducer mounted within said pod assembly with means for transmitting and receiving ultrasonic waves with the surface area of said transducer being substantially greater than the cross-sectional area of said needle.

9. The needle and syringe assembly as defined in claim 8 including means for directing the ultrasonic waves from said transducer through said needle.

10. The needle and syringe assembly as defined in claim 9 wherein said directing means includes a curved lens means positioned adjacent to said transducer.

11. The needle and syringe assembly as defined in claim 8 wherein said transducer is mounted between separable portions of said pod assembly and said transducer being configured to permit fluid communication between said syringe means and said needle.

* * * * *